United States Patent [19]
Webb

[11] Patent Number: 6,019,726
[45] Date of Patent: Feb. 1, 2000

[54] CATHETER HAVING PROBES FOR CORRECTING FOR NON-UNIFORM ROTATION OF A TRANSDUCER LOCATED WITHIN THE CATHETER

[75] Inventor: Peter Webb, Menlo Park, Calif.

[73] Assignee: Hewlett-Packard Company, Palo Alto, Calif.

[21] Appl. No.: 09/096,016

[22] Filed: Jun. 10, 1998

[51] Int. Cl.[7] .......................................................... A61B 8/14
[52] U.S. Cl. .......................... 600/459; 600/462; 600/463
[58] Field of Search .................................... 600/459, 463, 600/466, 445, 467, 454, 447, 462; 310/40 MM

[56] References Cited

U.S. PATENT DOCUMENTS

| | | |
|---|---|---|
| 4,794,931 | 1/1989 | Yock . |
| 4,917,097 | 4/1990 | Proudian et al. . |
| 5,000,185 | 3/1991 | Yock . |
| 5,176,141 | 1/1993 | Bom et al. . |
| 5,186,177 | 2/1993 | O'Donnell et al. . |
| 5,226,847 | 7/1993 | Thomas, III et al. ................... 600/467 |
| 5,240,003 | 8/1993 | Lancee et al. . |
| 5,271,402 | 12/1993 | Yeung et al. . |
| 5,284,148 | 2/1994 | Dias et al. . |
| 5,485,845 | 1/1996 | Verdonk et al. . |
| 5,503,155 | 4/1996 | Salmon et al. ........................... 600/459 |
| 5,507,294 | 4/1996 | Lum et al. . |
| 5,509,418 | 4/1996 | Lum et al. . |
| 5,699,805 | 12/1997 | Seward et al. ........................... 600/462 |
| 5,699,806 | 12/1997 | Webb et al. . |

Primary Examiner—Marvin M. Lateef
Assistant Examiner—Ali M. Imam

[57] ABSTRACT

A catheter for imaging a cavity. The catheter includes a sheath having a distal end that is introduced into a cavity to be imaged and a proximal end that resides outside of the cavity. The sheath includes a tubular member with a first fixed probe located proximate to the distal end and fixed in relation to the tubular member while the cavity is being imaged. The catheter also includes a transducer for delivering an energy pulse in a predetermined direction relative to the transducer and collecting echoes generated by the pulse. The transducer is located within the sheath proximate to the distal end of the sheath and includes a transducer probe affixed to the transducer. A drive cable in the catheter causes the transducer and the transducer probe to rotate relative to the sheath. The drive cable connects the transducer to a mechanical drive mechanism located at the proximate end of the sheath. A tracking circuit measures the electrical coupling between the transducer probe and the first fixed probe to determine the location of the transducer relative to the sheath.

14 Claims, 2 Drawing Sheets

CATHETER HAVING PROBES FOR CORRECTING FOR NON-UNIFORM ROTATION OF A TRANSDUCER LOCATED WITHIN THE CATHETER

FIELD OF THE INVENTION

The present invention relates to the generation of ultrasound images from mechanical rotating catheters, and more particularly, to an improved catheter that corrects for image distortion due to the non-uniform rotation of the catheter.

BACKGROUND OF THE INVENTION

Ultrasonic imaging is widely used in medicine because it does not subject the subject to ionizing radiation and is considerably less expensive than systems based on magnetic resonance imaging. In one application of ultrasound imaging, a probe containing an ultrasonic transducer is inserted into the body area to be imaged. The transducer transmits an acoustic pulse into the body tissues, and detects the reflections of the pulse at tissue boundaries due to differences in acoustic impedance, as well as the backscattered sound from acoustically heterogeneous tissue. The differing times taken for the transducer to receive the reflected and backscattered ultrasound correspond to the differing distances of the tissues from the transducer. By stepping or sweeping the transducer through a set of selected angles, a two-dimensional ultrasound image corresponding to a map of the acoustic impedance boundaries and backscattering coefficients can be obtained. From this image, the condition of the body tissues can be determined. For example, the method of intravascular ultrasound (IVUS) sequentially transmits ultrasound pulses in equally spaced increments around all or part of a circle to obtain cross-sectional images of blood vessels, most often coronary arteries demonstrating areas of atherosclerotic plaque, calcification, etc.

Generally, there are two types of ultrasonic probes for IVUS imaging. The first type employs a synthetic aperture technique. For example, U.S. Pat. No. 4,917,097 (Proudian, et al.) and U.S. Pat. No. 5,186,177 (O'Donnell, et al.) teach probes based on synthetic apertures. Generally, these probes utilize the sequential excitation of selected elements in an array of transducer elements to generate a sound pulse traveling in a particular direction which is determined by the elements excited and the relative phases of the excitation signals applied thereto.

The second type of IVUS probe scans the tissue by mechanical rotation of a transducer that emits pulses in a predetermined direction. The mechanically rotated type includes a few subclasses. In the first subclass, either a distal (remote from the operator) transducer or a mirror is rotated from the proximal end of the catheter by an extended drive shaft with a proximal motor (U.S. Pat. Nos. 4,794,931 and U.S. Pat. No. 5,000,185 (Yock)). In the second subclass, the rotation is confined to the distal end, where either a miniature motor (U.S. Pat. No. 5,240,003 (Lancee, et al.) and U.S. Pat. No. 5,176,141 (Bom, et al.)) or a fluid driven turbine is used to rotate the transducer or the mirror (U.S. Pat. No. 5,271,402 (Yeung and Dias)). In a third subclass, a stationary proximal transducer is acoustically coupled to a rotating acoustic waveguide that conducts the sound to the distal end (U.S. Pat. No. 5,284,148 (Dias and Melton)). In a fourth subclass (U.S. Pat. No. 5,509,418 (Lum, et al.)), a turbine is rotated by an acoustic signal generated outside the vessel to direct another ultrasonic signal in a rotating fashion. In the final subclass (U.S. Pat. No. 5,507,294 (Lum, et al.)), an external driving member rotates a tube to rotate a reflecting element at the tip of the tube to reflect ultrasound.

Presently, probes that direct ultrasonic pulses by mechanical rotation are more widely used than probes that electronically aim the pulses. The mechanical approach can be implemented using a single transducer, while the electronic approach requires an array of transducers to be contained in the distal end. Accordingly, the array requires a larger catheter. In many applications such as imaging blood vessels, minimizing the size of the catheter is essential.

Mechanical probes, however, can introduce distortions into the images resulting from uncertainties in the speed of rotation of the transducer. Typically, the distal end of the probe is assumed to rotate at a constant speed and ultrasound pulses are transmitted at regular time intervals. The angular position of each scan line is assumed to change by the same amount between each successive pulse. If, however, the angular rotation is not uniform, the angular positions of the scan lines corresponding to the various pulses will be in error and the resulting image will be distorted.

One cause of non-uniform angular velocity in the type of catheter that uses a driveshaft is the existence of mechanical friction between the spinning driveshaft and the surrounding stationary sheath. The catheter must bend numerous times through the tortuous path involved in placing the distal end at the desired location by traversing a blood vessel. Although the proximal end of the catheter is rotating at the desired angular velocity, any binding of the catheter along its length will lead to a distal angular velocity that is different from the desired velocity at various points of the full circle. The average velocity will be the same at the proximal and distal ends, and thus the distal end will sometimes be rotating too quickly, and sometimes too slowly. In general, the error is observed to be substantially the same on subsequent revolutions of the catheter. Thus, the image generated appears to be distorted even when large numbers of measurements are made.

Techniques for correcting for non-uniform rotation have been proposed. For example, U.S. Pat. No. 5,485,845 (Verdonk, et al.) describes a technique for detecting the non-uniform angular velocity of IVUS transducers by using an array of beacons positioned on the sheath. This approach determines the average angular velocity of the transducer between each pair of beacons. The accuracy of this approach is determined by the number of beacons and the placement thereof. To obtain high accuracy, large numbers of beacons are needed. However, the beacons can interfere with the image since the beacons form "bright" spots and shadows on the image. This interference increases with the number of beacons.

U.S. Pat. No. 5,699,806 (Webb, et al.) describes a technique for calculating the non-uniformity from the distorted images. This technique depends on the statistical distribution of the speckle pattern observed in ultrasound images of backscattering tissue. This pattern is absent in some imaging situations. For example, at the branch point between two blood vessels, there may be a region in which no reflected signal is obtained. Similarly, if the blood vessel has a calcified region, the strong reflection from the calcified region may interfere with the reflections and scattering generated by the tissue behind the calcified region, and hence, the detection of the angular velocity of the transducer.

Broadly, it is the object of the present invention to provide an improved ultrasound catheter and calibration method.

It is a further object of the present invention to provide an ultrasound catheter whose angular position can be determined without obstructing portions of the image.

It is a still further object of the present invention to provide an ultrasound imaging system that does not depend on the statistical properties of the image to determine the angular position of the transducer.

These and other objects of the present invention will become apparent to those skilled in the art from the following detailed description of the invention and the accompanying drawings.

SUMMARY OF THE INVENTION

The present invention is a catheter for imaging a cavity. The catheter includes a sheath having a distal end that is introduced into a cavity to be imaged and a proximal end that resides outside of the cavity. The sheath includes a tubular member with a first fixed probe located proximate to the distal end and fixed in relation to the tubular member while the cavity is being imaged. The catheter also includes a transducer for delivering an energy pulse in a predetermined direction relative to the transducer and collecting echoes generated by the pulse. The transducer is located within the sheath proximate to the distal end of the sheath and includes a transducer probe affixed to the transducer. A drive cable in the catheter causes the transducer and the transducer probe to rotate relative to the sheath. The drive cable connects the transducer to a mechanical drive mechanism located at the proximate end of the sheath. A tracking circuit measures the electrical coupling between the transducer probe and the first fixed probe to determine the location of the transducer relative to the sheath. In one embodiment, the tracking circuit measures the inductive coupling between the transducer probe and the first fixed probe. In this embodiment, the probes can be constructed from conducting loops. The inductive coupling of the loops is measured by applying a signal to one loop and measuring the signal amplitude induced in the other loop. In another embodiment, the catheter includes a second fixed probe located proximate to the distal end and fixed in relation to the tubular member, and the tracking circuit also measures the electrical coupling between the second fixed probe and the transducer probe.

DETAILED DESCRIPTION OF THE INVENTION

Figure 1:
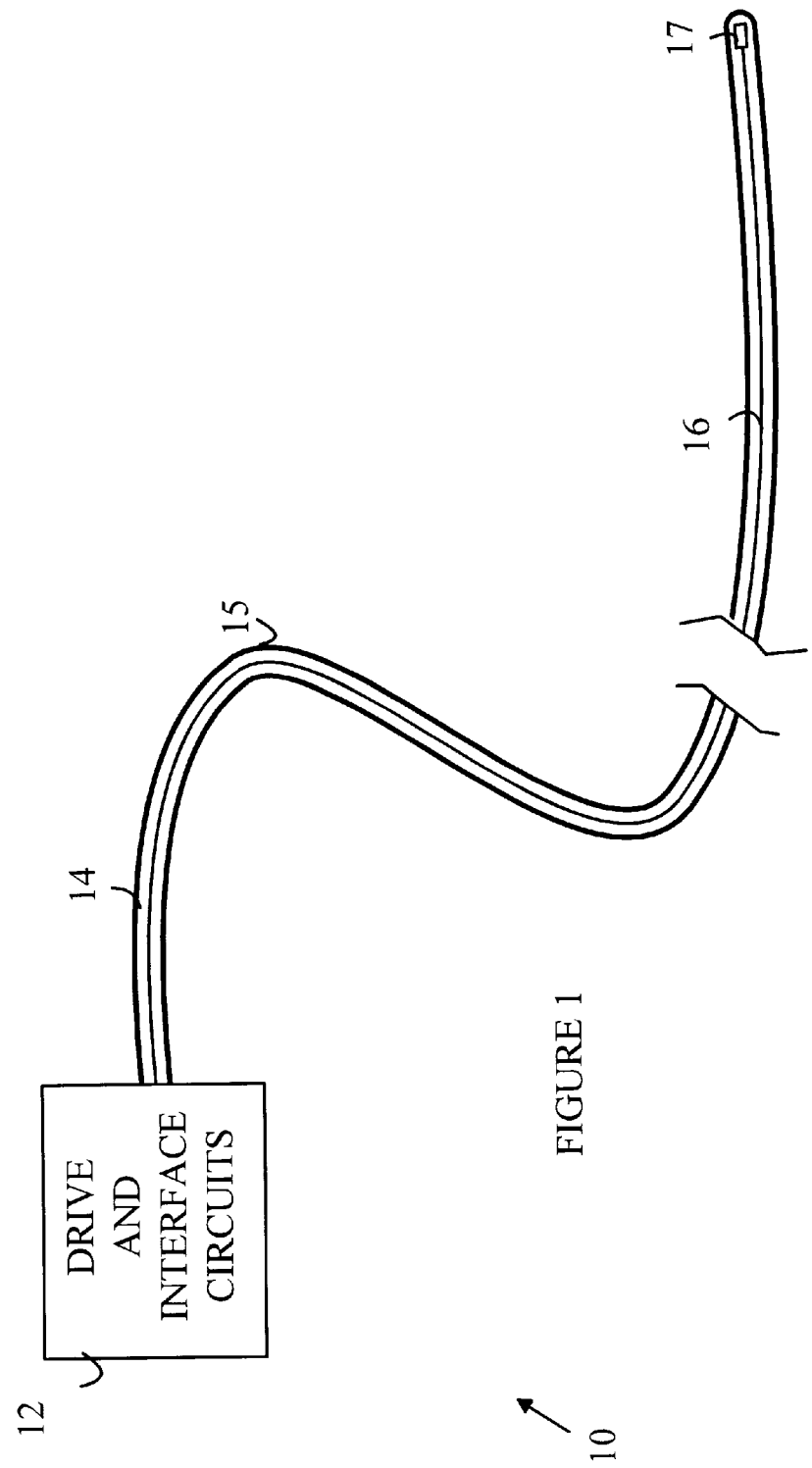
FIG. 1 is a schematic drawing of a catheter assembly 10 according to the present invention.

The present invention may be more easily understood with reference to FIG. 1, which is a schematic drawing of a catheter assembly 10 according to the present invention. Assembly 10 includes a catheter 14 having an outer sheath 15 and an inner drive cable 16. The distal end of catheter 14 is inserted into the cavity to be imaged. An ultrasound transducer 17 is mounted on the distal end of drive cable 16. Drive cable 16 is connected to interface circuitry 12, which provides the necessary signals to transducer 17. Drive cable 16 also rotates within sheath 15 thereby causing transducer 17 to rotate. Drive cable 16 includes the various signal conductors used to transmit signals to, and receive signals from, transducer 17.

To image the tissue surrounding the distal end of catheter 14, the transducer 17 radiates ultrasonic pulses in a sequential manner as transducer 17 rotates. The transmitted ultrasonic pulses are reflected and scattered by the tissues. The reflected acoustical signals are received by the transducer 17, which converts the acoustical energy into an electrical signal that is transmitted to interface 12.

As noted above, one problem with conventional catheters is the uncertainty in the position of transducer 17. While the end of drive cable 16 at the drive circuitry is rotated at a constant angular velocity, and its angular position can readily be measured, the distal end typically moves in a non-constant manner due to the friction between drive cable 16 and sheath 15. When catheter 14 is inserted into a blood vessel, it must bend to accommodate the various bends in the blood vessel. At the various points along the catheter at which the catheter is bent, the drive cable rubs against the fixed sheath. The present invention provides a detector at the distal end of catheter 14, which provides a signal indicative of the angular position of transducer 17 with respect to the fixed catheter sheath.

Figure 2:
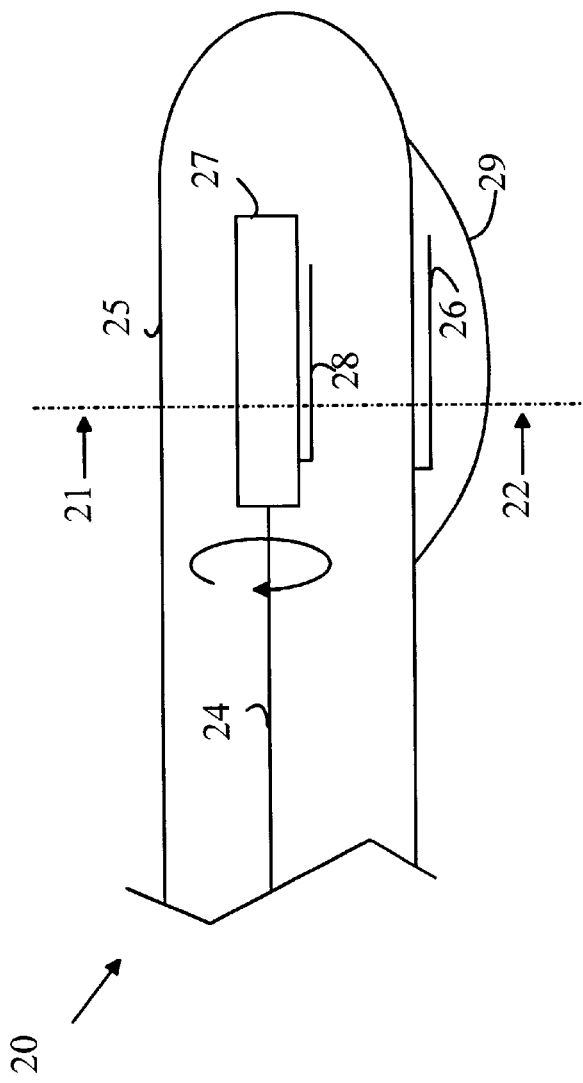
FIG. 2 is a cross-sectional view of the distal end of a catheter according to the present invention.
Figure 3:
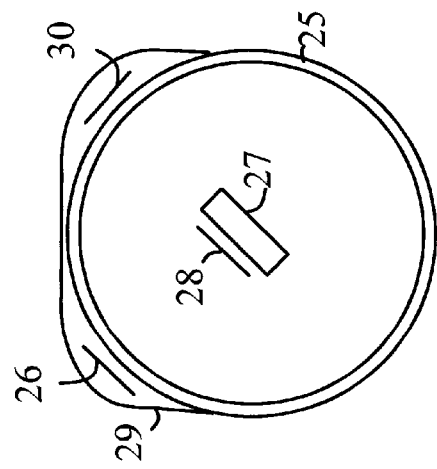
FIG. 3 is a cross-sectional view of the catheter shown in FIG. 2 through line 21–22.

The manner in which the detection scheme utilized in the present invention operates may be more easily understood with reference to FIGS. 2 and 3. FIG. 2 is a cross-sectional view of the distal end 20 of a catheter according to the present invention. The cross-section shown in FIG. 2 is taken along the drive cable 24. FIG. 3 is a cross-sectional view of catheter 20 through line 21–22 shown in FIG. 2. A transducer according to the present invention may be viewed as including a conventional ultrasound transducer 27 to which a coil 28 has been affixed. Coil 28 includes a conducting loop defining a plane. Coil 28 is affixed to transducer 27 and rotates therewith. The sheath 25 of catheter 20 includes a reference coil 26. By measuring the magnetic coupling between coils 26 and 28, the relative orientation of transducer 27 and reference coil 26 may be determined. When the planes of the coils are parallel to one another, the coupling is at its maximum. When the planes of the coils are at right angles to one another, the coupling is at its minimum.

Since the planes of the coils will be parallel to one another at two points in the rotation cycle, there is an ambiguity as to the location of the drive coil at the start of the measurements. Accordingly, in the preferred embodiment of the present invention, a second reference coil 30 is also present.

In the preferred embodiment of the present invention, the plane of the second coil is orthogonal to that of the first coil. By measuring the coupling of both coils 26 and 30 with coil 28, any uncertainty in the position of transducer 27 with respect to sheath 25 can be resolved.

Figure 4:
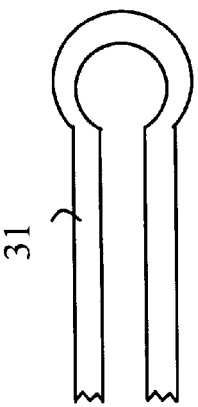
FIG. 4 illustrates a conductive loop suitable for use in constructing the probes shown in FIGS. 2–3.

The coils used to make the position measurements can be plated on the transducer and sheath. A single loop such as shown in FIG. 4 at 31 is sufficient. The coils on the sheath are protected from shorting by an insulating layer 29.

In the preferred embodiment of the present invention, the coupling between rotating coil 28 and the fixed reference coils is measured by observing the signal generated in coil 28 when RF signals are applied to coils 26 and 30. By applying signals of different frequencies to coils 26 and 30, the coupling of coils 26 and 28 can be measured simultaneously with that of coils 30 and 28.

In the preferred embodiment of the present invention, the coupling measurements are made between the ultrasound measurements. Typically, the time needed to send an ultrasound pulse and detect the echoes is much smaller than the time needed for the transducer to rotate to the next position at which an ultrasound measurement is to be made. During the transit of the transducer between each of the angular positions at which ultrasound measurements are to be made, the electronics in the interface circuitry that generate the ultrasound pulse and detect the echoes therefrom are idle. In the preferred embodiment of the present invention, these electronics are shared by the position sensing system during the period in which the electronics are not being used to make an ultrasound measurement.

To effectively utilize the ultrasound pulse electronics to also determine the position of the transducer with respect to the reference coils, the frequencies at which the coupling measurements are made must be close to that at which the ultrasound pulse is generated. For example, in the preferred embodiment of the present invention, the ultrasound pulse is generated at a frequency of 30 MHz and the coupling measurements are made at 25 and 35 MHz. This provides sufficient frequency separation to easily separate the coupling signals while assuring that the signals are within the range of the amplifiers and oscillators that are part of the ultrasound system transmitter/receiver electronics.

The above embodiments of the present invention have utilized the inductive coupling between one or more fixed coils on the catheter sheath and a coil that rotates with the ultrasound transducer. However, it will be obvious to those skilled in the art from the preceding discussion that other forms of probes can be utilized. For example, a system based on the capacitive coupling between a plate on the rotating transducer and one or more fixed plates on the sheath could likewise be utilized to determine the position of the rotating transducer.

Once the position of the transducer relative to the fixed sheath is accurately known, the ultrasound image may be corrected for the non-uniform motion of the transducer. In systems in which the transducer is pulsed at regular time intervals, the position data is used to assign the correct angular position to the echoes from each pulse. This leads to an image that is sampled in a non-uniform pattern. Alternatively, the position data can be utilized to trigger the ultrasound pulse at each desired angular position. In this case, the image will be uniformly sampled.

While the transducer locating system of the present invention has been described in terms of an ultrasound catheter, it will be obvious to those skilled in the art from the preceding discussion that the tracking system of the present invention may be utilized with other types of catheters. For example, imaging systems based on short light pulses are known. Such systems operate by generating a short light pulse and then detecting the backscattered light signals generated by the pulse. A catheter for applying this imaging technique in a cavity of a patient is structurally analogous to the ultrasound catheter described above. Such a catheter includes a rotating element that emits the energy pulse and detects the returned "echoes". The transducer is rotated by a drive a cable which, in this case, may include optical fibers for conducting the initial light pulse and collected light "echoes" to and from the distal end of the catheter. A rotating mirror at the distal end of the catheter determines the direction that light is emitted. An imaging lens collects the light echoes and directs the collected light back down the optical fiber. The rotating mirror and associated imaging lens is analogous to the ultrasound transducer discussed above.

The above-described embodiments of the present invention utilize reference probes that are attached to the sheath of the catheter. However, the present invention will operate satisfactorily with any reference probe that has a fixed relationship to the cavity being imaged. For example, one or more reference probes can be placed on the outside of the patient's body in the vicinity of the cavity being imaged.

Various modifications to the present invention will become apparent to those skilled in the art from the foregoing description and accompanying drawings. Accordingly, the present invention is to be limited solely by the scope of the following claims.

What is claimed is:

1. A catheter comprising:
   a sheath having a distal end that is introduced into a cavity to be imaged and a proximal end that resides outside of said cavity, said sheath comprising a tubular member with a first fixed probe located proximate to said distal end and fixed in relation to said tubular member while said cavity is being imaged;
   a transducer for delivering an energy pulse in a predetermined direction relative to said transducer and collecting echoes generated by said pulse, said transducer being located within said sheath proximate to said distal end of said sheath, said transducer further comprising a transducer probe affixed to said transducer;
   a drive cable for causing said transducer and said transducer probe to rotate relative to a sheath, said drive cable connecting said transducer to a mechanical drive mechanism located at the proximate end of said sheath; and
   a tracking circuit for measuring electromagnetic coupling between said transducer probe and said first fixed probe.

2. The catheter of claim 1 wherein said first fixed probe is located outside of said cavity.

3. The catheter of claim 1 wherein said transducer emits an ultrasound pulse.

4. The catheter of claim 1 wherein said transducer emits an electromagnetic pulse.

5. The catheter of claim 1 wherein said tracking circuit measures the inductive coupling between said transducer probe and said first fixed probe.

6. The catheter of claim 5 wherein said first fixed probe and said transducer probe each comprise a conductive loop.

7. The catheter of claim 1 wherein said tracking circuit measures the capacitive coupling between said transducer probe and said first fixed probe.

8. The catheter of claim 7 wherein said first fixed probe and said transducer probe each comprise a conductive layer.

9. The catheter of claim 1 further comprising a second fixed probe located proximate to said distal end and fixed in relation to said tubular member, wherein said tracking circuit also measures said electromagnetic coupling between said second fixed probe and said transducer probe.

10. The catheter of claim 3 wherein said transducer generates said pulse at a first frequency and wherein said tracking circuit measures said electromagnetic coupling between said first fixed probe and said transducer probe by applying a signal at said first frequency to one of said probes and detecting a signal at said frequency received by the other of said probes.

11. The catheter of claim 10 wherein said first frequency is greater than 10 KHz.

12. The catheter of claim 10 wherein said transducer probe is driven at a transducer frequency and detects signals at said transducer frequency using a receiving circuit and wherein said electromagnetic coupling between said first fixed probe and said transducer probe is detected by said receiving circuit.

13. The catheter of claim 12 wherein said electromagnetic coupling is detected when said receiving circuit is not used in image formation.

14. The catheter of claim 1 wherein said tracking circuit determines the angular position of said transmitter probe relative to said fixed probe.

* * * * *